United States Patent
Schwenker et al.

(10) Patent No.: US 11,369,319 B2
(45) Date of Patent: Jun. 28, 2022

(54) METHOD OF OPERATING A RECEIVER FOR RECEIVING ANALYTE DATA, RECEIVER AND COMPUTER PROGRAM PRODUCT

(71) Applicant: Roche Diabetes Care, Inc., Indianapolis, IN (US)

(72) Inventors: Kai-Oliver Schwenker, Hassloch (DE); Carsten Mueglitz, Schoenau (DE); Andreas Huber-Toth, Mannheim (DE); Felix Bootz, Speyer (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 800 days.

(21) Appl. No.: 16/088,307

(22) PCT Filed: Mar. 29, 2017

(86) PCT No.: PCT/EP2017/057437
§ 371 (c)(1),
(2) Date: Sep. 25, 2018

(87) PCT Pub. No.: WO2017/167815
PCT Pub. Date: Oct. 5, 2017

(65) Prior Publication Data
US 2020/0281538 A1    Sep. 10, 2020

(30) Foreign Application Priority Data

Mar. 29, 2016 (EP) .................................... 16162661
Mar. 28, 2017 (EP) .................................... 17163229

(51) Int. Cl.
*G08B 21/04* (2006.01)
*A61B 5/00* (2006.01)
(Continued)

(52) U.S. Cl.
CPC ........ *A61B 5/7275* (2013.01); *A61B 5/14532* (2013.01); *A61B 5/746* (2013.01); *G16H 50/30* (2018.01); *H01Q 1/27* (2013.01)

(58) Field of Classification Search
CPC .................................. A61B 1/00; G16H 10/00
(Continued)

(56) References Cited

U.S. PATENT DOCUMENTS 6,958,705 B2  10/2005  Lebel et al.
8,562,587 B2  10/2013  Kovatchev et al.
(Continued)

FOREIGN PATENT DOCUMENTS

CN    104520862    4/2015
CN    104755025    7/2015
(Continued)

OTHER PUBLICATIONS

David A. Gough et al: "Frequency Characterization of Blood Glucose Dynamics", Annals of Biomedical Engineering, vol. 31, No. 1, Jan. 1, 2003, pp. 91-97.
(Continued)

*Primary Examiner* — Daniel Previl
(74) *Attorney, Agent, or Firm* — Woodard, Emhardt, Henry, Reeves & Wagner, LLP

(57) ABSTRACT

The disclosure refers to a method of operating a receiver for receiving analyte data from a biosensor monitoring an analyte by detecting analyte values, the method comprising: in a receiver (1), receiving analyte values detected by a biosensor (8) monitoring an analyte in intervals of time for which a first interval time is applied; receiving a present analyte value in the receiver (1); providing a rate of change for the analyte values; determining a future analyte value based on the present analyte value, the first interval time, and the rate of change; providing an analyte value range for the
(Continued)

Figure 1:
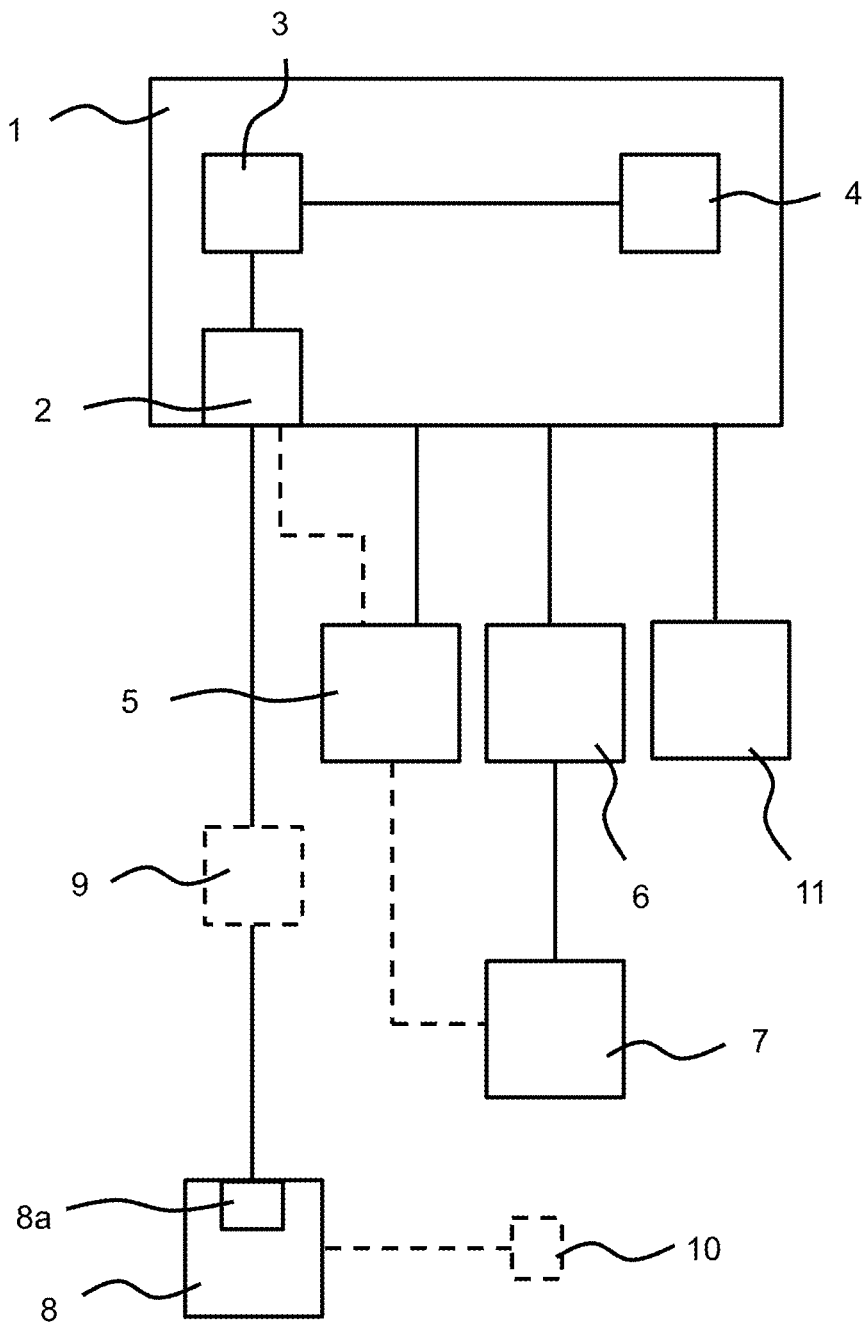

analyte values; setting a second interval time, the second interval time being shorter than the first interval time, if the future analyte value is outside the analyte value range, and longer than or equal to the first interval time, if the future analyte value is within the analyte value range; and in the receiver (1), receiving one or more following analyte values in intervals of time for which the second interval time is applied. Also, a receiver (1) is provided, comprising a receiver unit (2), and a processor (3) connected to the receiver unit (2). Further, a computer program product is provided.

20 Claims, 6 Drawing Sheets

(51) Int. Cl.
  *G16H 50/30* (2018.01)
  *A61B 5/145* (2006.01)
  *H01Q 1/27* (2006.01)

(58) Field of Classification Search
  USPC .... 340/539.12, 539.17, 539.29, 539.24, 575, 340/5.52, 5.82, 286.07
  See application file for complete search history.

(56) References Cited

U.S. PATENT DOCUMENTS

| | | | |
|---|---|---|---|
| 8,822,903 B2 | 1/2014 | Jin et al. | |
| 2009/0118592 A1* | 5/2009 | Klitgaard | A61B 5/6849 600/300 |
| 2011/0077494 A1* | 3/2011 | Doniger | A61B 5/746 600/365 |
| 2012/0065482 A1* | 3/2012 | Robinson | A61B 5/150389 600/309 |
| 2012/0085482 A1 | 3/2012 | Robinson et al. | |
| 2012/0197222 A1 | 8/2012 | Donnay et al. | |
| 2014/0046159 A1 | 2/2014 | Kovatchev et al. | |
| 2014/0148659 A1* | 5/2014 | Sloan | A61B 5/7221 600/309 |
| 2015/0123810 A1 | 5/2015 | Hernandez-Rosas et al. | |
| 2015/0216457 A1* | 8/2015 | Kasahara | A61B 5/14532 600/316 |

FOREIGN PATENT DOCUMENTS

| | | |
|---|---|---|
| CN | 105208933 | 12/2015 |
| EP | 2 011 283 B1 | 11/2009 |
| EP | 2 748 747 A1 | 7/2014 |
| JP | 2015142665 | 8/2015 |
| JP | 2016005585 | 1/2016 |
| JP | 2016027460 | 2/2016 |
| WO | WO 01/60248 | 6/2001 |
| WO | WO 2008/057384 | 5/2008 |
| WO | WO 2010/091028 A1 | 8/2010 |
| WO | WO 2011/026053 | 3/2011 |
| WO | WO 2013/032965 | 3/2013 |
| WO | WO 2014/018926 A1 | 1/2014 |
| WO | WO 2015/094981 A1 | 6/2015 |

OTHER PUBLICATIONS

Christian Kotanen, "Implantable biosensors for physiologic status monitoring during hemorrage" (2013). All Dissertations. 1162.

* cited by examiner

METHOD OF OPERATING A RECEIVER FOR RECEIVING ANALYTE DATA, RECEIVER AND COMPUTER PROGRAM PRODUCT

The present disclosure refers to a method of operating the receiver for receiving analyte data, a receiver, and a computer program product.

BACKGROUND

Glucose monitoring helps people with diabetes manage the disease and avoid its associated problems. A person can use the results of glucose monitoring to make decisions about food, physical activity, and medications. A common way to check glucose level is performing discontinuous monitoring. Such checking usually involves pricking a fingertip with an automatic lancing device to obtain a blood sample and then using a glucose meter to measure the blood sample's glucose level. Such monitoring may also be referred to as spot monitoring.

As an alternative or in addition, continuous glucose monitoring (CGM) may be applied. A system for CGM may use a body sensor inserted under the skin to check glucose levels. The sensor stays in place for several days to weeks and then must be replaced. A transmitter sends information about an analyte value or level indicative of the glucose level via wireless and/or wired data transmission from the sensor to a receiver such as monitor device.

Document WO 2015/094981 A1 discloses a method for prolonging life of a battery installed in an analyte sensor system. The method includes measuring a first analyte value at a first time and causing a transmission of the measured first analyte value along with a predicted second analyte value. Measure a second analyte value at a second time and determine whether a difference between the measured second analyte value and the predicted second analyte value is within a predefined range. Skip transmission of the measured second analyte value if the difference is within the predefined range.

Document US 2009/0118592 A1 discloses a medical system comprising a sensor unit and a receiving unit. The sensor unit is adapted to generate sensor data indicative of a time-dependent characteristic of a subject, and transmit data to a receiver at intervals determined by an analysis of time-dependent changes in the generated sensor data. The receiving unit is adapted to receive sensor data at a non-predetermined rate. By this arrangement sensor data can be transmitted only when considered necessary in accordance with a predetermined strategy, thus reducing the energy consumption associated with the transmission of data. The strategy may set out that the transmission of sensor data is skipped in case there is no or only a small change in an actual sensor data value. On the other hand, in case of rapid changes in sensor data values, sensor data may be transmitted at higher rate.

Document EP 2 011 283 B1 discloses a method for wireless transmission of data between components of a blood glucose system by initially setting the receiver activation frequency to a first frequency value upon switching from communication mode to power saving mode, and setting the receiver activation frequency to a second frequency value smaller than the first frequency value if no communication initiation data frame is received for a predetermined power saving timeout period. The communication initiation data frame is transmitted such that the preamble period exceeds the length of the cycle duration corresponding to the first frequency value, and, in case no response is received by the controller during the response period, the communication initiation data frame is adapted and retransmitted such that the preamble period is increased and exceeds the length of the cycle duration corresponding to the second frequency value.

Document U.S. Pat. No. 8,622,903 B2 discloses a monitoring system with a transmitter configured to transmit once every minute randomly in a window of time of plus or minus 5 seconds, i.e. it time hops. To conserve power receiver does not listen for its associated transmitter during the entire 10 second receive window, but only at the predetermined time it knows the data packet will be coming from the corresponding transmitter.

Document U.S. Pat. No. 6,958,705 B2 discloses a medical system, comprising an ambulatory medical device (MD) with a MD telemetry system and a communication device (CD) with a CD telemetry. The CD telemetry system sends messages to or receives messages from the MD telemetry system, wherein at least one of the medical device and the communication device comprises a plurality of electronic modules, wherein at least one of the modules is at least a portion of the time switched from an active state to a power saving state when not in use and switched again to an active state when needed, and wherein the at least one MD processor applies power and clocking signals to the plurality of electronic modules on an as needed basis.

SUMMARY

It is an object of the present disclosure to provide a method of operating a receiver for receiving analyte data and a receiver for which the operation in the process of collecting analyte data is improved. Specifically, energy or power consumption shall be reduced in the arrangement comprising the receiver and the biosensor.

According to the present disclosure, a method of operating a receiver for receiving analyte data and a receiver are provided according to the independent claims 1 and 14, respectively. Further, a computer program product is provided according to claim 15. Alternative embodiments are disclosed in the dependent claims.

According to an aspect of the present disclosure, a method of operating a receiver for receiving analyte data from a biosensor monitoring an analyte by detecting analyte values is provided. The method comprises: receiving analyte values detected by a biosensor monitoring an analyte in intervals of time for which a first interval time is applied in a receiver; receiving a present analyte value in the receiver; providing a rate of change for the analyte values, determining a future analyte value based on the present analyte value, the first interval time, and the rate of change, and providing an analyte value range for the analyte values. A second interval time is set, the second interval time being shorter than the first interval time, if the future analyte value is outside of the analyte value range, and the second interval time being longer than or equal to the first interval time, if the future analyte value is within the analyte value range. In the receiver, one or more following analyte values are received in intervals of time for which the second interval time is applied.

According to another aspect, a receiver is provided comprising a receiver unit, and a processor connected to the receiver unit. The processor is configured to receive, through the receiver unit, analyte values detected by a biosensor monitoring an analyte in intervals of time for which a first interval time is applied; receive a present analyte value;

provide a rate of change for the analyte values; determine a future analyte value based on the present analyte value and the first interval time, and the rate of change and provide an analyte value range for the analyte values. A second interval time is set. The second interval time is shorter than the first interval time, if the future analyte value is outside the analyte value range, and the second interval time is longer than or equal to the first interval time, if the future analyte value is within the analyte value range. Wire the receiver one or more following analyte values are received in intervals of time for which the second interval time is applied.

According to a further aspect, a computer program product is provided.

The determining of the future analyte value based on the present analyte value, the first interval time, and the rate of change may be referred to as extrapolation.

At least one of the providing the rate of change for the analyte values, determining the future analyte value, providing an analyte value range for the analyte values, and setting the second interval time may be performed or implemented in the receiver. As an alternative, one or more of such steps may be implemented in a remote control device connect to the receiver and, optionally, to the biosensor for data transmission. It may also be foreseen to configure the handheld or portable device comprising the receiver to control the biosensor and/or some other medical device such as a drug delivery pump.

The first of the following analyte values may be the next analyte value to be received after the present analyte value is received. As an alternative, the first of the following analyte values can be received after one or more additional analyte values have been received following the step of receiving the present analyte value.

The determining of the future analyte value and the steps to follow in response to it may be done for each analyte value received by the receiver.

The rate of change may indicate a possible increase (positive rate of change) or a possible decrease (negative rate of change) in time.

The rate of change provided for the analyte values in the receiver may be a maximum rate of change. As an alternative or in addition, a minimum rate of change may be provided to be used in the setting the second interval time. The maximum rate of change and/or the minimum rate of change may be a maximum physiological rate of change and/or a minimum physiological rate of change, respectively. For example, in an embodiment of glucose monitoring, an averaged maximum physiological rate of change for the glucose level of about 5 mg/dl/min may be applied. The physiological rate of change may be a personalized or patient specific physiological rate of change for a patient.

The analyte value range may be set in response to receiving a user input, thereby, the user can be provided with control of the interval time defining the time period between successive events of receiving one or more analyte values in the receiver. For example, the user may define the first and second threshold value by user input, thereby defining the analyte value range referring to analyte values in a range from the first to the second threshold value. The user input may be received in the receiver.

The analyte value range may be a pre-defined analyte value range. With regard to glucose level measurement, the pre-defined value range may range from a lower limit of 40 to 90 mg/dl or from 50 to 80 mg/dl to an upper limit of 140 to 200 mg/dl or 160 to 180 mg/dl.

The first and second interval times each define a time period between successive events of receiving analyte value(s) in the receiver. Such receiving may be receiving a single analyte value detected by the biosensor. As an alternative, a series of analyte values detected by the biosensor before may be received in such event. The analyte values of the group of analyte values may be processed in the receiver, e.g. for determining an average analyte value or a median value.

The first and second interval times may define time intervals being equal, such equal or even time intervals being characterized by the same time interval between successive events of receiving analyte value(s) in the receive.

In the biosensor, a time stamp may be assigned to each of the analyte values sent to the receiver, the time stamp indicating an individual sample time for the respective analyte value. The sample time refers to a point in time at which the analyte value was sensed or generated by the biosensor. A sample time period may be defined, the sample time period defining the time period between successive events of sensing an analyte value by the biosensor. Information on the sample time period may be provided in the receiver.

The one or more following analyte values received in the receiver may comprise at least an analyte value sensed or generated most recently by the biosensor. The receiver may analyze time stamp information for the analyte values received. Once the receiver determines that a time interval between the point in time indicated by the time stamp assigned to the most recent analyte value and the point in time indicated by the time stamp assigned to the analyte value received latest before the most recent analyte value is larger than the first or second interval time, the receiver may request the biosensor to transmit the lacking analyte values sensed or generated in such intermediate time period between detecting the most recent analyte value and the analyte value received latest before the most recent analyte value.

The analyte values may be received by one of wireless data communication and wired data communication in the receiver. The receiver may be provided with a transceiver unit connected to a processor. The processor may be configured for data processing such as at least one of the analyte values, the analyte value range, and the rate of change for the analyte values.

The receiver may be provided in a mobile device such as a handheld device, a laptop, a mobile phone, and smart watch and a remote controller. The receiver may be configured to control operation of a medical system such as a drug delivery medical system. As an alternative, the receiver may be provided in a non-mobile device such as a desktop computer.

The processor may be connected to an output device such as a display for a displaying at least one of the present analyte value, the rate of change for the analyte values, the analyte value range, the one or more following analyte values, and one of the first and second interval times. The receiver may be provided with a power supply connected at least to the receiving unit and the processor. If the display is present, the power supply may be connected to the display device as well.

The biosensor may be configured for monitoring an analyte in a bodily fluid. For example, a glucose value of a bodily fluid may be monitored. However, the technologies disclosed may be used with regard to other analytes as well.

The processor may be provided with machine readable instructions to implement the method of operating the receiver for receiving the analyte data from the biosensor.

The receiving of the analyte values may comprises receiving analyte values detected by the biosensor in a continuous analyte monitoring. The analyte values sensed in the continuous analyte monitoring may be received periodically in the receiver. As an alternative, the receiving of the analyte values may comprises receiving analyte values in an intermittent/non-continuous monitoring. The user may trigger the transfer of the analyte values, and the biosensor measures continuously. In such an embodiment the data indicative of the analyte values from the biosensor are received by the receiver on demand of the user. The analyte values are received aperiodically.

The method may further comprise receiving analyte values detected by the biosensor in a present monitoring sequence; and determining the analyte value range from analyte values detected by the biosensor in a past monitoring sequence different from the present monitoring sequence. With regard to this or other embodiments, analyzing past monitoring may also be referred to as retrospective analysis. The past monitoring sequence or series, for example, providing for a continuous or non-continuous/discontinuous analyte monitoring may be finished before the present monitoring sequence is started. For example, the present and the past monitoring sequences may be done on different days. As an alternative, the present and the past monitoring sequences may be done at different day times such as morning and afternoon. Also, it may be foreseen to have the past and the present monitoring sequences done in different weeks, but on the same week day. At least one of a maximum and a minimum analyte value range may be determined from the analysis of the analyte values detected by the biosensor in the past monitoring sequence.

The providing of the rate of change may comprise providing a rate of change selected from the following group: a present rate of change, a maximum physiologically possible and clinically (empirically) determined rate of change, and a patient specific rate of change for the analyte values. The patient specific rate of change which may also be referred to as personalized rate of change may have been determined from a different kind of analyte measurement. For example, the rate of change for a glucose level for a patient may be determined from a blood glucose measurement, while the analyte values are detected by the biosensor which is present in e.g. the interstitium. The analyte value may be measured in an interstitial fluid. The glucose measurement may be performed subcutaneously. The measurement in interstitial fluid is indicative of a blood glucose level. A continuous glucose monitoring may be foreseen which may be implemented as a nearly real-time or quasi-continuous monitoring procedure frequently or automatically providing/updating analyte values without user interaction.

The providing of the rate of change may comprise determining the rate of change from analysis of the analyte values detected by the biosensor in the past monitoring sequence. At least one of a maximum and a minimum rate of change may be determined from the analysis of the analyte values detected by the biosensor in the past monitoring sequence or series (retrospective analysis). The maximum rate of change and/or the minimum rate of change determined from the past monitoring may be a maximum physiological rate of change and/or a minimum physiological rate of change, respectively. From the analysis of the past monitoring sequence, a personalized or patient specific rate of change may be determined for the patient. In such alternative embodiment, the past monitoring and the present monitoring may be performed for the same patient. The rate of change information determined from the past monitoring sequence may comprise data indicative of at least one of a patient specific maximum physiological rate of change and a patient specific minimum physiological rate of change.

The providing of the rate of change may comprise selecting a rate of change value from a group of rate of change values, each of the rate of change values indicating a rate of change for the analyte values. For example, in the receiver different rate of change values may be provided in dependence on the day time (morning, afternoon). Also, different rate of change values may apply depending on an activity of a patient, such as sleeping or physical exercise. The rate of change may differ for a person working in the office and the person doing some physical exercise like sport. The selecting can be based on at least one of daily segments (night/day), patient specific patterns, and specifically behavioral patterns.

The method may further comprise determining a decision parameter, and selecting the rate of change value based on the decision parameter. The decision parameter, for example, may define at least one of a daily segment, a daytime, an event such as a meal, and a physical status of a person such physical activity, sport, illness, and stress. In addition or as an alternative, a physical state of the person (patient) may be taken into account as decision criteria, such as, for example, illness and/or stress. The rate of change values may be the same for decision parameters differing from each other. For example, in a specific case the rate of change may be the same for a day time parameter assigned to the morning and the afternoon, respectively. In an alternative embodiment, a different rate of change may be assigned to differing decision parameters. For example, the maximum rate of change physiological feasible (maximum physiological rate of change) and/or the minimum rate of change physiological feasible (minimum physiological rate of change) may be different for different decision parameters, e.g., different times of the day (morning, evening; daytime, nighttime). In an example, a lower maximum rate of change may apply to daytime compared to nighttime. In response to providing different limits for the rate of change, the determining of the interval times will lead to a dynamic adjustment process. In addition or as an alternative, the maximum rate of change physiological feasible and/or the minimum rate of change physiological feasible may be selected in dependence on at least one of a physical activity of a person (patient) and some other event such as insulin take.

The setting of the second interval time may comprise determining a parameter of revision defining when at least one of the following steps is to be performed next time: determining the future analyte value, and setting the second interval time. In addition to setting the second interval time the parameter of revision defines further aspects of receiving the future analyte values in the receiver. For example, the parameter of revision may define a number of analyte values to be received prior to the next determination of the future analyte value and the further setting of the second interval time. As an alternative or in addition, the parameter of revision may define a time period until the next determination of the future analyte value and the following step is performed. The revision parameter may define a maximum time interval for which no connection is allowed between the biosensor and the receiver, for example, thereby implementing a safety measure.

In response to detecting an event, a current analyte value may be received from the biosensor. The event may be a user input received in the receiver. For example, such user input may refer to activating an output device of the receiver, e.g., a display, and/or starting a software application such as an analyte value analysis tool in the receiver. Receiving the analyte values in intervals of time for which the first or the second interval times are set may provide for regularly receiving analyte values in the receiver. In response to detecting an event a current analyte value may be received from the biosensor, such receiving of the current analyte value not being within the mode of the regular analyte value transmission to the receiver.

In response to detecting the event, the receiving of the analyte values in intervals of time for which the first or second interval times apply may be interrupted. Transmitting the current analyte value from the biosensor to the receiver in response to detecting the event will interrupt the regular transmission mode. After the current analyte value is received, the regular transmission mode for which the first or second interval times are applied may be resumed. As an alternative, the setting of the second interval time may be done in response to receiving and analyzing the current analyte value as outlined above.

The receiving of the current analyte value may further comprise receiving the current analyte value in a background process non-interrupting the receiving of the analyte values in intervals of time for which the first or second interval times are applied. The background process may be performed without interfering with the regular transmission mode for which the first or second interval times are applied. Before and after receiving the current analyte value the regular mode of transmission is continued. The background process may be performed by the receiver without notifying the user of the receiver about the receiving of the current analyte value.

The detecting of the event may further comprise detecting at least one of a user input by at least one of the receiver and a control device connected to the receiver, and a sensor signal by a sensor connected to the receiver. The control device may receive a user input through an input unit of the control device. The control device may be provided with a processor connected to the input unit. The control device may be provided together with the receiver in a mobile or non-mobile device. For example, a user input may be received via a keyboard or a touch sensitive display. For example, the user may initiate the transmission of the current analyte value by providing the user input. As an alternative or in addition, current analyte values may be received in the receiver in response to a sensor signal. For example, the sensor may be a light sensor for detecting daylight, thereby, providing information on present daylight/day time. As an alternative or in addition, sensor signals may be provided by a microphone, a accelerometer, and/or a camera. Also, a sensor detecting movement and/or acceleration for the receiver may be provided. As an alternative, the user may provide information on an event such as physical activity and/or meal taking by a user input. Such or other information may be processed by the processor of the receiver for determining the rate change value.

The method may further comprise: determining, based on at least one of the future analyte value, the rate of change, and the second interval time, whether a control parameter is exceeding a control parameter threshold, and, if the control parameter is exceeding the control parameter threshold, receiving one or more following analyte values from the biosensor in the receiver, wherein the one or more following analyte values are received within an amended interval time which is shorter than the second interval time. At least one of the future analyte value, the rate of change, and the second interval time may be processed for determining the control parameter which to be compared to the control parameter threshold. Thereby, it may be avoided that the second interval time determined is in conflict with some additional requirement optionally to be applied in the method of operation the receiver for receiving analyte data from the biosensor.

The setting of the second interval time may comprise setting a time period between successive events of device connecting between the receiver and the biosensor, wherein the device connecting comprises establishing a connection for data transmission between the receiver and the biosensor. The first and second interval times each may define a time period between successive events of establishing the device connection. A first device connecting process may include an initial process referred to as device pairing, the device pairing may comprise establishing a secure and encrypted connection for data transmission between the receiver and the biosensor. The establishing or setting-up of the connection (communication channel) configured for secure and encrypted data transmission may comprise exchanging keys for secure data exchange (secure keys) between the two devices. After the initial device pairing has been completed, reconnection may be done without repeating device pairing or key exchange. Re-connecting comprises establishing the connection which may also be referred to as communication channel between the biosensor and the receiver again after the connection was interrupted or stopped, for example, during the time period between successive events of data transmission defined by the time intervals. Following, after the establishing of the connection the analyte values detected by the biosensor may be received in the receiver. In an embodiment, control signals may be transmitted from the receiver to the biosensor, the control signals defining a time delay between the end of the device connection process and the starting point of transmitting the one or more analyte values to the receiver. As an alternative, with regard to the first and/or the second interval times, the time period can be determined in relation to the point in time at which the former transmission of the one or more analyte values was started.

Following, alternative aspects are described with regard to the determining of the control parameter.

For example, the second interval time may provide for the control parameter. Such control parameter may be compared to a maximum interval time (control parameter threshold) provided in the receiver, for example, by user input. If the second interval time determined is longer than the maximum interval time, transmission of the one or more following analyte values may be performed earlier, for example, after lapse of the maximum interval time which is shorter than the second interval time.

In an alternative embodiment or in addition, there may be a software algorithm or module controlling the control parameter and outputting a warning signal if it is found that the control parameter is exceeding the control parameter threshold. The transmission of the one or more following analyte values may be started in such case prior to the end of the second interval time, if the warning signal is to be outputted.

Prior to determining the control parameter based on the extrapolated value(s) such as at least one the future analyte value and the second interval time, the control parameter (current control parameter) may be determined based on current values such as at last one of the present analyte value and the first interval time. Following, the current or present control parameter may be stored in a memory of the receiver.

In addition or as an alternative, a copy of the software module configured to determine the control parameter and to compare it to the maximum control parameter may be stored in the memory of the receiver.

Contrary, the control parameter determined based on the extrapolated value(s) may be omitted from storing in the memory of the receiver, thereby, saving storage capacity. It may be foreseen to delete electronic data related to the determining of the control parameter and the comparing of the control parameter to the maximum control parameter after such comparison in the receiver.

In an alternative embodiment, the control parameter may be provided as the result of a method or process, e.g. a method or process for determination applied to at least one value. The values may include any of the following: analyte value received, rate of change of analyte values, period of time consecutively received analyte value stay within or outside a certain analyte value range, amount of administered basal or bolus insulin over a certain period of time, etc. The method or process may be any method applied in the field of diabetes management including:
a) method suitable to determine the risk of the glucose analyte value to be outside a certain glucose concentration range within a certain window of time;
b) method suitable to determine the risk of the glucose analyte value to be in the hypoglycemic concentration range within a certain window of time;
c) method suitable to determine an insulin bolus of basal rate suitable to change the patient's glucose concentration such that it develops to a glucose concentration within a certain concentration range within certain window of time; and
d) method suitable to determine a temporary stop or reduction of the currently administered basal rate preferably suitable to change the patient's glucose concentration preferably such that it develops to a glucose concentration within a certain concentration range within certain window of time.

Embodiments of such methods or processes and corresponding values processed by the method or process, corresponding control parameter thresholds, and corresponding warnings triggered can be used in the technologies disclosed here and are disclosed as such, for example, in U.S. Pat. No. 8,562,587 B2, EP 2 748 747 A1, WO 2008/057384, and US 2014/0046159 A1.

With regard to a glucose measurement or monitoring, a glucose level or value may be determined by analyzing a blood sample via e.g. spot monitoring, and, as an alternative or in addition, by continuous glucose monitoring (CGM) via a fully or partially implanted sensor. In general, in the context of CGM an analyte value or level indicative of a glucose value or level in the blood may be determined. The analyte value may be measured in an interstitial fluid. The measurement may be performed subcutaneously or in vivo. CGM may be implemented as a nearly realtime or quasi-continuous monitoring procedure frequently or automatically providing/updating analyte values without user interaction. In an alternative embodiment, analyte may be measured with a biosensor in a contact lens through the eye fluid or with a biosensor on the skin via transdermal measurement in sudor.

The alternative embodiments described above may apply to the receiver mutatis mutandis.

In an alternative embodiment, a method of operating a receiver for receiving analyte data from a biosensor monitoring an analyte by detecting analyte values may be provided. The method comprises: providing analyte values such as glucose levels detected by a biosensor monitoring an analyte at different points in time in a receiver; providing a rate of change for the analyte values, for example, a rate of change for the glucose level; determining present analyte values exceeding a first threshold analyte value or level; measuring, after one or more of the present analyte values exceed the first threshold analyte value, the period of time the present analyte values remain above the first threshold analyte value but below a second threshold analyte value; defining a transmission point in time for a next event of receiving further or following analyte values detected by the biosensor in the receiver based on a reference analyte value selected from the present analyte values, the rate of change, and the period of time.

The first and second threshold analyte values may be defined or set based on user input received in the receiver. The transmission point, for example, may be determined by defining an amended or new interval time for receiving analyte values from the biosensor on the receiver. Such interval time may be applied for a single event of receiving analyte values or a series of events of receiving analyte values. With regard to such alternative method, the embodiments described above may apply mutatis mutandis.

The alternative embodiments of the user defined transmission of the analyte values from the biosensor to the receiver provide to the user control of the energy consumption of the receiver. Specifically, in response to the user input, the frequency of analyte value transmission to the receiver may be controlled. The user may determine the transmission of the analyte values to the receiver to be performed more or less frequently by user input.

The intervals of time applied to the receiving of analyte values in the receiver, in general, may be limited to be no longer than about 10 min. In an alternative embodiment, a time limit of about 20 min may be applied, or, in another alternative embodiment, a time limit of about 30 min may be applied. An upper limit may be set for the interval of time in the receiver. The upper limit may be provided in response to a user input in the receiver. The upper limit may be a user specific upper time limit.

In an alternative embodiment, a method of operating a receiver for receiving analyte data from a biosensor monitoring an analyte by detecting analyte values is provided. The method is comprising: in a receiver, receiving analyte values detected by a biosensor monitoring an analyte in intervals of time for which a first interval time is applied; receiving a present analyte value in the receiver; providing a rate of change for the analyte values; determining a future analyte value based on the present analyte value, the first interval time, and the rate of change; and, in response to determining the future analyte value, setting a second interval time which is different from the first interval time. Further, after determining the second interval time, it is determined whether a control parameter is exceeding a control parameter threshold. If the control parameter is exceeding the control parameter threshold, one or more following analyte values are received from the biosensor in the receiver, wherein the one or more following analyte values are received within an amended interval time which is shorter than the second interval time. The amended interval time may be different from the first interval time as well.

With regard to the control parameter, it may be provided as the result of a method or process as described for the alternative embodiments in the present disclosure.

DESCRIPTION OF FURTHER EMBODIMENTS

Figure 2:
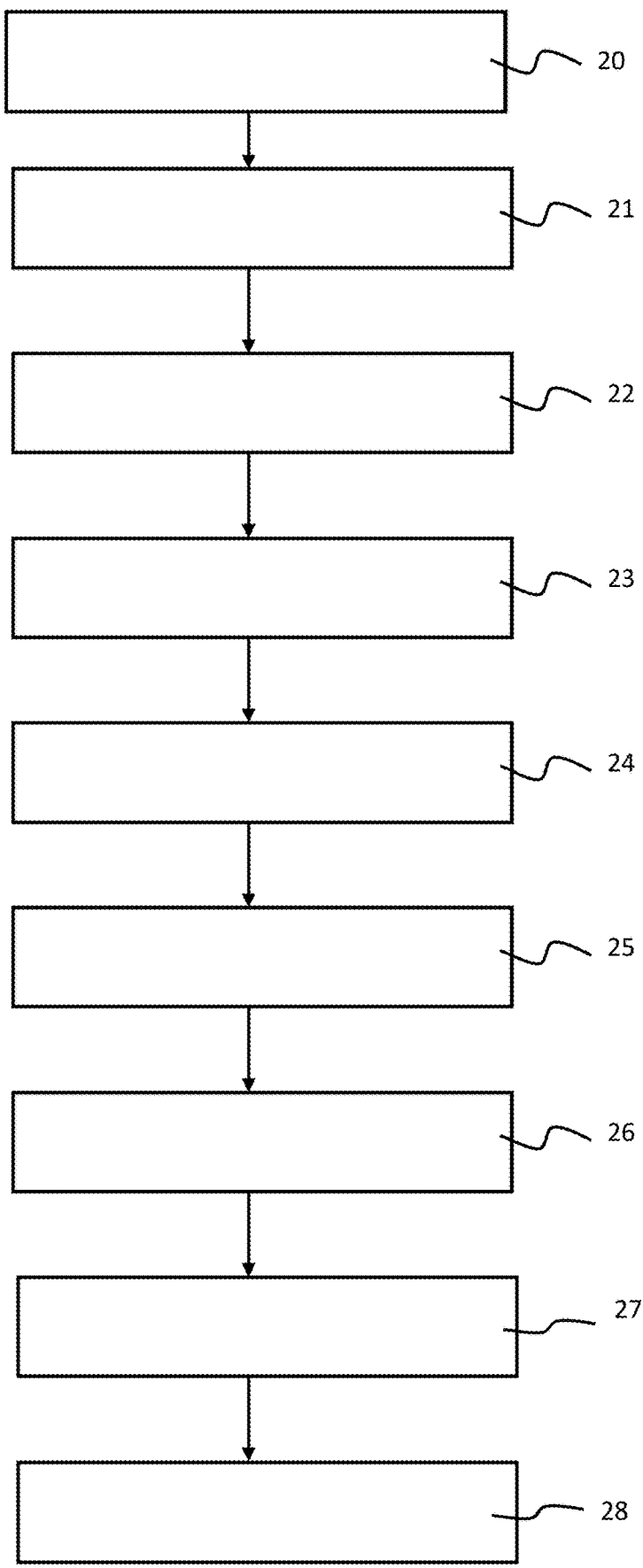
Figure 3:
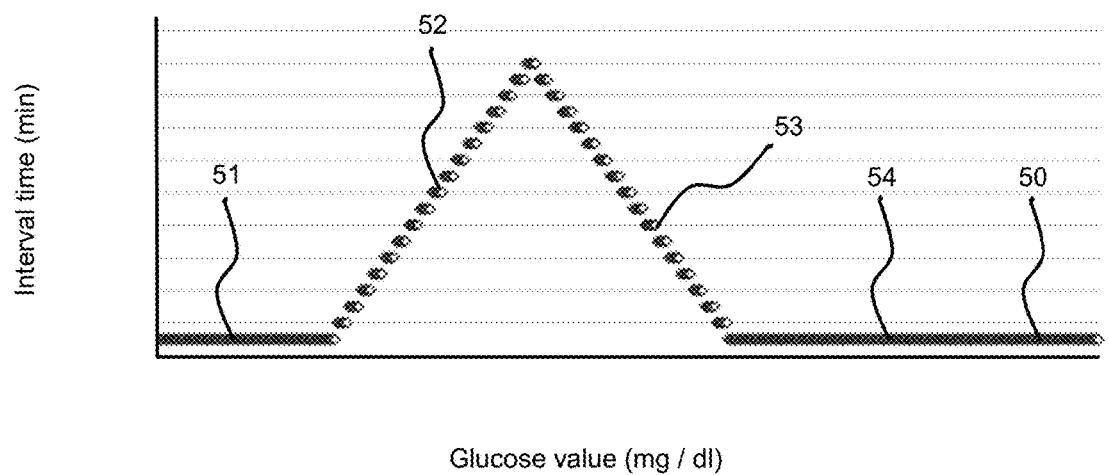
Figure 4:
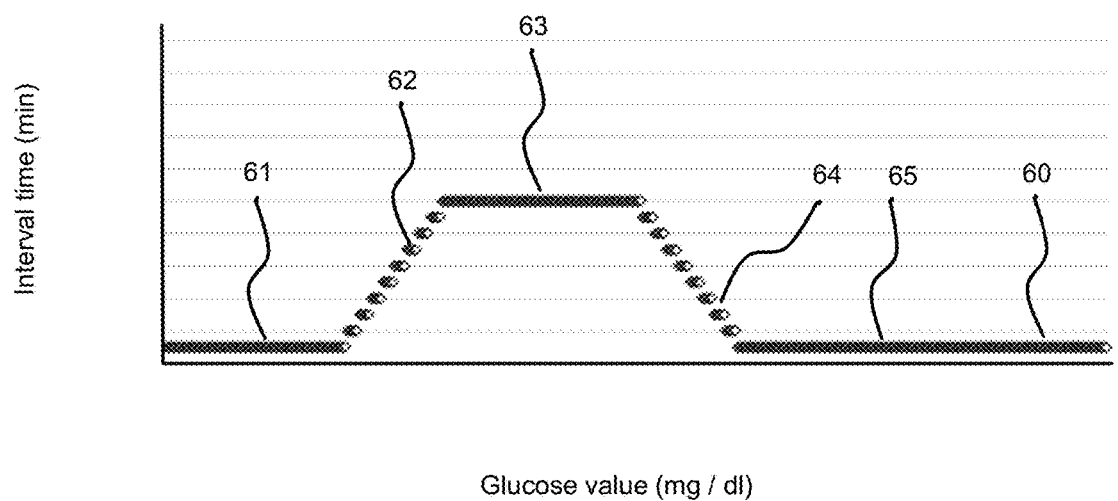
Figure 5:
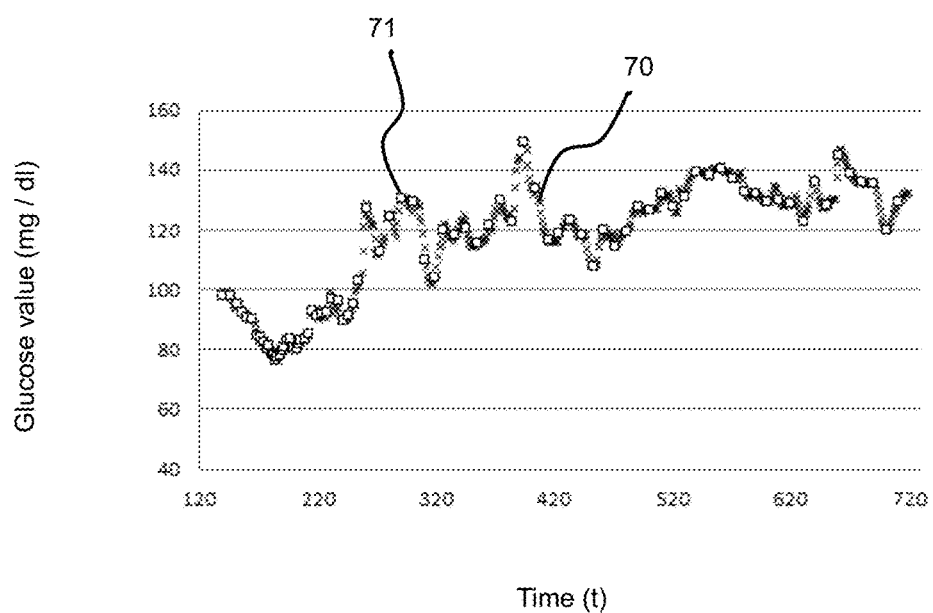
Figure 6:
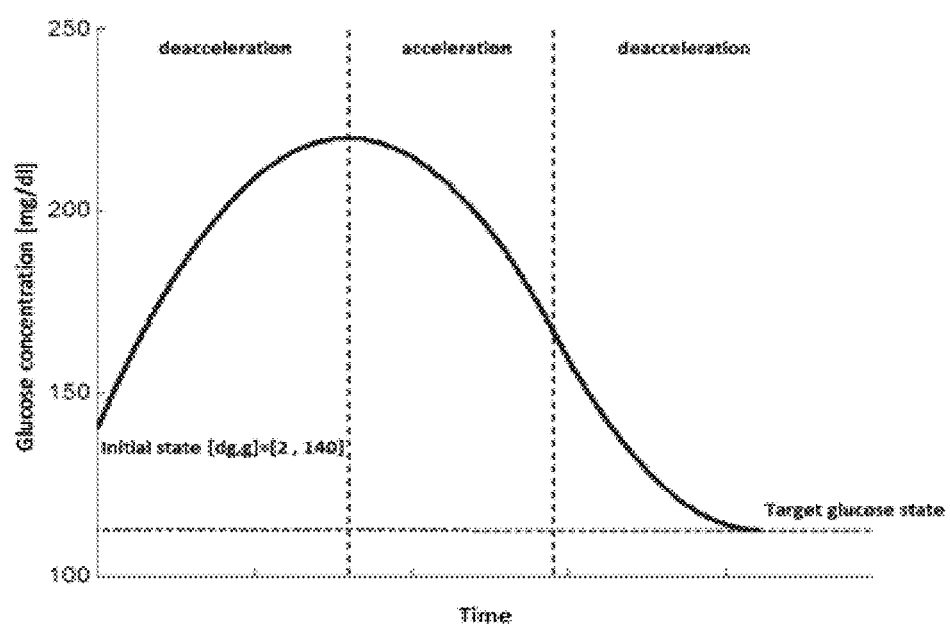

Following, embodiments, by way of example, are described with reference to figures. In the figures show:

FIG. 1 a schematic representation of a medical system provided with a biosensor and a receiver;

FIG. 2 a schematic representation with regard to a method of operating a receiver for receiving analyte data or values from the biosensor monitoring an analyte;

FIG. 3 a graphical representation of an interval time in dependence on a present glucose value;

FIG. 4 a further graphical representation the interval time in dependence on a present glucose value;

FIG. 5 a schematic representation of analyte values received in the receiver in dependence on time; and FIG. 6 a schematic graphical representation of the glucose concentration over time.

FIG. 1 generally depicts an embodiment of a system for automatically analyzing analyte monitoring data indicative of a glucose level. The system generally comprises a receiver 1 provided with a transceiver unit 2 and a processor 3. As an alternative, a plurality of processors may be provided. The transceiver unit 2 connected to the processor 3 comprises a data interface configured to receive and transmit electronic data. Also, the receiver 1 comprises a memory 4 connected to the processor 3 for storing electronic data such as machine readable instructions, e.g., software applications. According to the embodiment shown in FIG. 1, the receiver 1 is optionally provided with an input device 5 configured to receive user input and an output device 6 configured for outputting electronic data, e.g., through a display. The input device 5 and the output device 6 may be implemented integrally with the receiver 1. For example, a common housing may be provided, the common housing comprising the receiver 1, the input device 5, and the output device 6. As an alternative, at least one of the input device 5 and the output device 6 may be separable from the receiver 1. In an alternative embodiment, an external transceiver configured for at least one of data input and data output through wireless data communication may by detachably connected to the receiver 1, e.g. through an USB port.

A human machine interface 7 is communicably coupled to the output device 6 and, optionally, the input device 5.

Machine readable instructions may be provided that are executed by the processor 3 for operating the receiver 1 in the system. Various embodiments of the system and methods for operating the receiver 1 will be described in more detail herein.

The processor 3 may be a controller, an integrated circuit, a microchip, a computer, or any other computing device capable of executing machine readable instructions. The memory 4 may be RAM, ROM, a flash memory, a hard drive, or any device capable of storing machine readable instructions.

In the embodiments described herein, the processor 3 may be integral with the receiver 1. However, it is noted that, if a plurality of processors is provided, such processors may be separately located within the receiver 1 and one or more further discrete components of the system such as, for example, a glucose meter, a medication delivery device, a mobile phone, a portable digital assistant (PDA), a mobile computing device such as a laptop, a tablet, or a smart phone, a desktop computer, or a server e.g. via a cloud or web based technologies and communicatively coupled with at least the receiver 1. It is to be appreciated that in at least one embodiment, such a device may include a touch screen and the computing ability to run computational algorithms and/or processes, such as those disclosed herein, and applications, such as an electronic mail program, a calendar program for providing a calendar, as well as provide cellular, wireless, and/or wired connectivity and one or more of the functions of a glucose meter, a digital media player, a digital camera, a video camera, a GPS navigation unit, and a web browser that can access and properly display web pages. Accordingly, the system may include a plurality of components each having at least one processor that is communicatively coupled with one or more of the other components. Thus, the system may utilize a distributed computing arrangement to perform any or the machine readable instructions described herein.

The system further comprises the human machine interface 7 communicatively coupled to the receiver 1 for receiving signals from the output device 6 and presenting graphical, textual and/or auditory information. The human machine interface 7 may include an electronic display such as, for example, a liquid crystal display, thin film transistor display, light emitting diode display, a capacitive or inductive touch screen, or any other device capable of transforming signals from a processor into an optical output, or a mechanical output, such as, for example, a speaker, a printer for displaying information on media, and the like.

Embodiments of the present disclosure may also comprise machine readable instructions that includes logic or an algorithm written in a programming language such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the logic or algorithm may be written in a hardware description language (HDL), such as implemented via either a field-programmable gate array (FPGA) configuration or an application-specific integrated circuit (ASIC), and their equivalents. Accordingly, the machine readable instructions may be implemented in any conventional computer programming language, as pre-programmed hardware elements, or as a combination of hardware and software components. Moreover, machine readable instructions can be distributed over various components that are communicatively coupled such as, for example, via wires, via a wide area network, via a local area network, via a personal area network, and the like. Thus, any components of the system can transmit signal over the Internet or World Wide Web.

Referring still to FIG. 1, the exemplary system depicted include a biosensor 8 communicatively coupled to the receiver 1 through the transceiver unit 2 for providing biological or analyte data indicative of properties of an analyte such as glucose. The transceiver unit 2 provides for a receiver-side transceiver. The biosensor 8 is provided with a sensor-side transceiver unit 8a configured for transmitting and receiving electronic data.

The biological or analyte data received in the receiver 1 at least in part may be stored in the memory 4. The biosensor 8 which may be provided as body sensor at least in part implantable into a human body can be coupled directly or via an intermediate device 9 to the transceiver unit 2. The intermediate device 9 may be configured to receive the measurement data (analyte values) from the biosensor 8 and to transmit the measurement data to the receiver 1 with or without processing the measurement data in the intermediate device 9 locally before transmission to the receiver 1. According to FIG. 1, the biosensor 8 may be connected to a remote control device 10. The remote control device 10 may be configured to control data transmission between the biosensor 8 and the receiver 1, optionally through the intermediate device 9. For example, the biosensor 8 can be activated/deactivated (turn ON/OFF) by the remote control 10. In an embodiment, the biosensor 8 may be disabled for sensing signals (turn OFF) by the remote control 10 for saving battery power. After activation (turn ON) the biosensor 8 is ready for sampling measurement data, such sampling may be controlled by the receiver 1. In another embodiment, the biosensor 8 may be disabled with regard to data transmission, but the sensor still being labeled for sensing measurement signals representing biological or analyte values.

In one embodiment, the biosensor 8 is a glucose sensor configured to detect or sense a glucose level (e.g., glucose concentration) when placed just under the skin of a patient. Specifically, a subcutaneously placed biosensor may be provided. For example, the biosensor 8 can be a disposable glucose sensor that is worn under the skin for a few days until replacement is needed. As is noted above, the biosensor 8 can be communicatively coupled with the receiver 1. Accordingly, in the case of a glucose sensor, the biosensor 8 can be communicatively coupled with, for example, a hand held device such as a smart phone or a remote controlling device, or a smart glucose meter and can provide ambulatory CGM data, i.e., glucose data that is sampled continuously throughout the lifetime of the sensor. The receiver 1 provided in the device controls the data transmission from the biosensor 8 to the handheld.

Referring to the schematic representation in FIG. 2, an embodiment of a method for operating the receiver 1 is described.

In step 20 the receiver 1 is provided and connected by a wireless and/or a wired data communication line to the biosensor 8 directly or indirectly through the intermediate device 9. The biosensor 8 is monitoring an analyte by detecting analyte values. The biosensor 8 may be in part or completely implanted under a skin of a patient. For example, the biosensor 8 may be configured for subcutaneously measuring the analyte concentration in an interstitial fluid.

Analyte values detected by the biosensor 8 monitoring the analyte are received in the receiver 1 in step 21. The analyte values are received in time intervals for which a first interval time is applied. The first interval time determines the time period between successive events of receiving one or more analyte values. The receiving may follow in response to a device connecting, such device connecting establishing a connection for (secure) data transmission (communication channel) between the biosensor 8 and the receiver 1. A connection capable of secure data transmission (secure connection; secure communication channel) may be established by exchanging keys between the biosensor 8 and the receiver 1.

In case of a first device connecting and prior to actually receiving one or more analyte values through the connection in the receiver 1, a so-called device pairing process is provided between the receiver 1 and the biosensor 8. The device pairing process is the initial process for establishing the connection for data transmission between the receiver 1 and the biosensor 8. By the pairing process a unidirectional or bidirectional data transmission line or connection is established between the devices. In response to finalizing the device pairing which is known as such, e.g. with regard to pairing Bluetooth devices, through the connection, the one or more analyte values may be transmitted immediately or in a timely delayed fashion from the biosensor 8 to the receiver 1.

The biosensor 8, e.g. through the sensor-side transceiver unit 8a, may by continuously sending a signal "ready for pairing". Such signal indicates that the biosensor 8 may be paired with some other device for transmitting data. In response to detecting the signal "ready for pairing", the receiver 1 may start the pairing process.

The one or more analyte values may be directly transmitted from the biosensor 8 to the receiver 1. In an alternative embodiment, the data transmission may optionally be provided through the intermediate device 9. If the intermediate device 9 takes part in the data transmission, device pairing may be conducted between the receiver 1 and the intermediate device 9 on one side and the intermediate device 9 and the biosensor 8 on the other side, thereby, establishing indirect data transfer from the biosensor 8 to the receiver 1 through the intermediate device 9.

With regard to both the data exchange related to the device pairing and the following transmission of data related to the one or more analyte values, encrypted data may be transmitted between the components such as the receiver 1, the biosensor 8 and, optionally, the intermediate device 9. For example, the data relating to the device pairing may not be encrypted, but the one or more analyte values may be transmitted by encrypted data.

The pairing process may be initiated by the receiver 1 in response to detecting the biosensor 8 in the vicinity or within a range of data transmission of the receiver 1. For example, the transceiver unit 2 may be provided with Bluetooth functionality comprising an observation function for detecting devices provided with Bluetooth functionality as well.

If the process of device pairing is present, the first interval time may determine the time period between successive events of device pairing followed by receiving one or more analyte values in the receiver 1. As an alternative, the first interval time may determine the time period between successive events of device connecting/re-connecting followed by receiving one or more analyte values in the receiver 1. Following the device pairing, the connection for data transmission between the biosensor 8 and the receiver 1 may be established or re-established without again performing device pairing.

The time period may be determined in relation to a point in time at which one of a former device pairing and a former device connecting was started. As an alternative, the time period may be determined in relation to a point in time at which a former event of transmitting analyte values from the biosensor 8 to the receiver 1 has ended, the former event comprising device pairing followed by receiving one or more analyte values in the receiver 1.

In an embodiment, control signals may be transmitted from the receiver 1 to the biosensor 8 which define a time delay between the end of the pairing process/device connecting process and the starting point of transmitting the one or more analyte values to the receiver 1. As an alternative, the time period may be determined in relation to the point in time at which the former transmission of the one or more analyte values was started.

The event of receiving analyte values, for example, may be triggered by a control mechanism provided in the receiver 1 and/or the remote control device 10. The control mechanism, at least in part, may be implemented by machine readable instructions.

In step 22 a present analyte value is received in the receiver 1. Further, a rate of change for the analyte values is provided in the receiver in step 23. Such rate of change characterizes possible change of the analyte values or the analyte level over time. In an embodiment, the rate of change may define a maximum rate of change, e.g. a physiologically feasible rate of change. The rate of change may be evaluated by the receiver 1 based on a series of most recent analyte values. Here the series may include e.g. the analyte values covering the most recent 15, 10, 5 or 2 minutes. The (fitted) slope connecting these analyte values gives the rate of change.

Based on the present analyte value, the first interval time, and the rate of change, in step 24, a future analyte value is determined or predicted. Such determination may include a projection of the present analyte value over a time corresponding to the first interval time via the rate of change (extrapolation). The first interval time providing for a prediction horizon, for example, may be 2, 5, 10 or 15 min.

In a step 26, such future analyte value is compared to an analyte value range provided in step 25 to the receiver 1. The analyte value range defines a possible or allowed range for the analyte values detected by the biosensor 8. Such analyte value range may be defined by a first and a second threshold. The analyte value range may define a lower and an upper limit for the analyte values, such lower and upper limit referring to a first and second threshold. In case of glucose measurement and analysis, the upper limit and the lower limit may refer to hyperglycemia and hypoglycemia, respectively. The analyte value range may be a patient specific analyte value range for the patient for whom the analyte values are collected by the biosensor 8.

The analyte value range may be set in response to receiving a user input, thereby, the user can be provided with control of the interval time defining the time period between successive events of receiving one or more analyte values in the receiver 1. For example, the user may define the first and second threshold value by user input, thereby defining the analyte value range referring to analyte values in a range from the first to the second threshold value. The user input may be received in the receiver 1.

In step 27, a second interval time is set. The second interval time is shorter than the first interval time, if the future analyte value is determined to be outside the analyte value range. As an alternative, the second interval time is longer than or equal to the first interval time, if the future analyte value determined before is within the analyte value range provided in the receiver 1. Depending on whether the predicted future analyte value is falling within or is outside the analyte value range, the second interval time is set different from the first interval time.

In step 28 one or more following analyte values are received in the receiver 1, wherein the following analyte values are received in intervals of time for which the second interval time is applied. Thereby, a procedure of dynamic transmission of the analyte values from the biosensor 8 to the receiver 1 may be implemented.

In the biosensor 8, a time stamp may be assigned to each of the analyte values sent to the receiver 1, the time stamp indicating an individual sample time for the respective analyte value. The sample time refers to a point in time at which the analyte value was sensed or detected by the biosensor 8. A sample time period may be defined, the sample time period defining the time period between successive events of sensing an analyte value by the biosensor 8. Information on the sample time period may be provided in the biosensor 8, and the receiver 1 as well.

The one or more following analyte values received in the receiver 1 may comprise at least an analyte value sensed most recently by the biosensor 8. The receiver 1 may analyze time stamp information for the analyte values received. Once the receiver 1 determines that a time interval between the point in time indicated by the time stamp assigned to the most recent analyte value and the point in time indicated by the time stamp assigned to the analyte value received latest before the most recent analyte value is larger than the first or second interval time, the receiver 1 may request the biosensor 8 to transmit missing (not transmitted) analyte values sensed in such intermediate time period between the detecting of the most recent analyte value and the detecting of the analyte value received latest before the most recent analyte value.

FIG. 3 shows a graphical representation of the dynamically changing interval time applied to the device connecting for data transmission between the biosensor 8 and the receiver 1 in dependence on a present glucose value. A curve 50 depicted is flat in a first range 51 indicating a constant interval time of 1 min which does not change. Following, in a second range 52 of the curve 50 the interval times are increasing from 1 min to 18 min, followed by a third range 53 characterized by decreasing interval times. In a fourth range 54 of the curve 50 the interval time is constant and short (1 min) again.

FIG. 4 shows a further graphical representation of the dynamically changing interval time applied to the device connecting for data transmission between the biosensor 8 and the receiver 1 in dependence on a present glucose value. A curve 60 depicted is flat in a first range 61 referring to low glucose values. The flat curve is indicating a constant interval time of 1 min which does not change. Following, in a second range 62 of the curve 60 the interval times are increasing, followed by a third range 63 characterized by a constant interval time of 10 min. In a fourth range 64 of the curve the interval times are decreasing, followed by constant interval times in a fifth range 65 of the curve.

FIG. 5 shows a graphical representation of a sequence of analyte values received over time in the receiver 1. First analyte values represented by a curve 70 are received in time intervals to which a fixed first interval time is applied. The first interval time has not been changed over the time of observation. In contrast, for a second sequence of analyte values represent by a curve 71 a dynamic second interval time was applied. The second interval time (dynamically) changes over the time of observation. The second interval time has been determined and set according to the aspect of the method described above.

Various embodiments may apply to the method of operating the receiver 1.

The receiving of the analyte values in intervals of time for which the first and the second interval times, respectively, are applied may be interrupted or stopped by manual user action. For example, a user input for interruption or stopping may be received through the input device 5. Also, in addition to the receiving of the analyte values in intervals of time in the receiver 1, manual transmission of analyte values may be triggered by user input. For example, a user input may trigger transmission of analyte values from the biosensor 8 to the receiver 1 in between two events of receiving analyte values in intervals of time. In response to the user input, a present device pairing process may be started followed by transmission of one or more analyte values from the biosensor 8 to the receiver 1.

The receiver 1 may be provided with a sensor 11. The sensor 11 may be configured to detect daylight. The sensor 11 may be provided with a camera and/or a microphone for detecting video signals and/or audio signals. Receiving such signals by the sensor 11 may trigger transmission of analyte values from the biosensor 8 to the receiver 1. In response to the sensor signal, a present device pairing process may be triggered followed by transmission of one or more analyte values from the biosensor 8 to the receiver 1. In addition or as an alternative, such sensor detection by the sensor 11 may interrupt or even stop receiving the analyte values in intervals of time in the receiver 1.

In an alternative embodiment, the sensor 11 may be configured to detect movement and/or acceleration of the receiver 1 or a device comprising the receiver 1.

As an alternative or in addition, by at least one the user input and the sensor input a process of switching form the first interval time to the second interval time may be initiated in the receiver 1. The second interval time may be set as outlined above in response. The second interval time is shorter than the first interval time, if the future analyte value is outside the analyte value range, and the second interval time is longer than the first interval time, if the future analyte value is within the analyte value range. With the receiver 1 one or more following analyte values are received in intervals of time for which the second interval time is applied.

Thereby, with regard to setting the second interval time, additional information or parameter(s) may be considered. For example, the second interval time, compared to the first interval time, may be extended or shortened in dependence on daytime (morning, afternoon, night). Also, patient specific information may be determined as outline above. In response to determination of such patient specific information, the second interval time may be shortened or extended further.

The rate of change applied in the step of determining the future analyte value in the receiver 1 may be determined from a previous sequence of analyte value monitoring. For example, a previous CGM measurement may be analyzed for determining a patient specific rate of change. A maximum rate of change may be determined in this and other embodiments. As an alternative or in addition, a minimum rate of change may be determined.

After determining the second interval time, the second interval time being determined according to one of the alternative embodiments described in the present disclosure, in a supplementary process, it may be determined whether a control parameter is exceeding a control parameter threshold, and, if the control parameter is exceeding the control parameter threshold, one or more following analyte values from the biosensor may be received in the receiver, wherein the one or more following analyte values are received within an amended interval time which is shorter than the second interval time.

The control parameter may be provided as the result of a method or process, e.g. a method or process for determination applied to at least one value. The values may include any of the following: analyte value received, rate of change of analyte values, period of time consecutively received analyte value stay within or outside a certain analyte value range, amount of administered basal or bolus insulin over a certain period of time, etc. The method or process may be any method applied in the field of diabetes management including: a) method suitable to determine the risk of the glucose analyte value to be outside a certain glucose concentration range within a certain window of time; b) method suitable to determine the risk of the glucose analyte value to be in the hypoglycemic concentration range within a certain window of time; c) method suitable to determine an insulin bolus of basal rate suitable to change the patient's glucose concentration such that it develops to a glucose concentration within a certain concentration range within certain window of time; and d) method suitable to determine a temporary stop or reduction of the currently administered basal rate preferably suitable to change the patient's glucose concentration preferably such that it develops to a glucose concentration within a certain concentration range within certain window of time. Embodiments of such methods or processes and corresponding values processed by the method or process, corresponding control parameter thresholds, and corresponding warnings triggered can be used in the technologies disclosed here and are disclosed as such, for example, in U.S. Pat. No. 8,562,587 B2, EP 2 748 747 A1, WO 2008/057384, and US 2014/0046159 A1.

FIG. 6 shows a schematic graphical representation of the glucose concentration over time. Following, with regard to an alternative embodiment for determining the control parameter from a method or algorithm, reference is made to the method of predictive Low Glucose Suspend (pLSG). The method for pLGS uses or processes a current state of the glucose level of a patient (glucose value and rate of change). Based on the current state, a possible or predictive way to a target glucose state of the patient's glucose level is determined (cf. FIG. 6). The risk of hypoglycemia is determined following the calculated path to the target glucose state. Based on the risk to get hypoglycemia, the insulin delivery is reduced in response.

For example, the following settings may be provided: Initial State—140 mg/dL; and rate of change—+2 mg/dL/min.

The steps to reach the target glucose state (110 mg/dL/0 mg/dL/min) are determined. In this exemplary case, the first step is to determine the glucose level in case the maximum acceleration applies. The maximum acceleration is a configurable parameter. After the maximum point of glucose concentration is determined, the path to the target glucose state is determined (cf. FIG. 6). The acceleration parameter is used to calculate the maximum decrease of glucose level in the body. With this the points of glucose level from the current glucose state to the target glucose state could be calculated.

The risk value of a single point is calculated by the formula (cf. Kovatchev et al., "Risk Analysis of Blood Glucose Data: A Quantitative Approach to Optimizing the Control of Insulin Dependent Diabetes", Journal of Theoretical Medicine, Vol. 3. Pp. 1-10):

$$r(bG)=10*[1.509*(\ln(bG)^{1.084}-5.381)]^2$$

The risk of a path from the current glucose state to the target glucose state is the integration of the risk values along the path.

In case the resulting risk value is higher than a predefined risk level, the risk value is converted to a Basal Rate Factor (0-1). This factor may be rounded to a value with one decimal. This rounded factor is applied to the current running Basal Rate on the insulin pump. In case the newly determined factor has not changed, the factor is not transmitted to the insulin pump (this will reduce the communication interval to the pump/here a push not a pull of data). The factor is determined as a control parameter and compared to the old factor (control parameter threshold) which has been applied before.

The second interval time for receiving analyte values in the receiver 1 which was determined before may be amended in response to comparing the old and the new factor. Specifically, it may be shortened for receiving next analyte values earlier. If, in an alternative embodiment, the second interval time has not been determined before, therefore, the first interval still being applied, the first interval time may be amended in response the finding about the factor determined by the pLGS method like it has been described for the second interval time (shortening). The resulting risk value is determined based on an extrapolation applying the current glucose state and the rate of change in the pLGS method.

The invention claimed is:

1. A method of operating a continuous analyte monitor including a receiver for receiving analyte data from a biosensor continuously monitoring an analyte by detecting analyte values, the method comprising:
the biosensor transmitting to the receiver, in intervals of time for which a first interval time is applied, analyte values detected by the continuous biosensor monitoring the analyte;
receiving present analyte values in the receiver;
providing a rate of change for the analyte values;
determining a future analyte value based on the present analyte values, the first interval time, and the rate of change;
providing an analyte value range for the analyte values;
setting a second interval time,
the second interval time being shorter than the first interval time if the future analyte value is outside the analyte value range, and
the second interval time being longer than or equal to the first interval time if the future analyte value is within the analyte value range; and
following the setting of the second interval time, transmitting from the biosensor to the receiver one or more following analyte values in intervals of time for which the second interval time is applied.

2. The method according to claim 1, further comprising receiving analyte values detected by the biosensor in a present monitoring sequence; and
determining the analyte value range from analyte values detected by the biosensor in a past monitoring sequence different from the present monitoring sequence.

3. The method according to claim 1, wherein the providing of the rate of change comprises providing a rate of change selected from the following group: a present rate of change, a maximum physiologically possible and clinically determined rate of change, and a patient specific rate of change for the analyte values.

4. The method according to claim 1, wherein the providing of the rate of change comprises determining the rate of change from analysis of the analyte values detected by the biosensor in the past monitoring sequence.

5. The method according to claim 1, wherein the providing of the rate of change comprises selecting a rate of change value from a group of rate of change values, each of the rate of change values indicating a rate of change for the analyte values.

6. The method according to claim 1, further comprising determining a decision parameter; and
selecting the rate of change value based on the decision parameter.

7. The method according to claim 1, wherein the setting of the second interval time comprises determining a parameter of revision defining when at least one of the following steps is to be performed next time: determining the future analyte value, and setting the second interval time.

8. The method according to claim 1, further comprising, in response to detecting an event, receiving a current analyte value from the biosensor.

9. The method according to claim 8, further comprising, in response to detecting the event, interrupting the receiving of the analyte values in intervals of time for which the first or second interval times are applied.

10. The method according to claim 8, wherein the receiving of the current analyte value further comprises receiving the current analyte value in a background process non-interrupting the receiving of the analyte values in intervals of time for which the first or second interval times are applied.

11. The method according to claim 8, wherein the detecting of the event further comprises detecting at least one of
a user input by at least one of the receiver and a control device connected to the receiver; and
a sensor signal by a sensor connected to the receiver.

12. The method according to claim 1, further comprising
determining, based on at least one of the future analyte value, the rate of change, and the second interval time, whether a control parameter is exceeding a control parameter threshold; and
if the control parameter is exceeding the control parameter threshold, receiving one or more following analyte values from the biosensor in the receiver, wherein the one or more following analyte values are received within an amended interval time which is shorter than the second interval time.

13. Non-transitory computer readable storage medium storing instructions that when executed perform the method of claim 1.

14. The method of claim 1 wherein the receiver includes a controller and a transmitter, the method including the controller determining the second interval time and controlling the biosensor to transmit the one or more following analyte values at the second interval time.

15. The method of claim 1 in which the analyte is glucose and the continuous analyte monitor is a continuous glucose monitor, and the method provides diabetes management for a subject.

16. The method of claim 15 and further including determining and administering an insulin bolus based on the determined analyte value.

17. The method of claim 15 and further including stopping or reducing a currently administered basal rate.

18. A continuous analyte monitoring system, comprising
a receiver unit, and
a processor connected to the receiver unit,
wherein the processor is configured to
receive, through the receiver unit, analyte values detected by a biosensor continuously monitoring an analyte in intervals of time for which a first interval time is applied;
receive, through the receiver unit, a present analyte value;
provide a rate of change for the analyte values;
determine a future analyte value based on the present analyte value, the first interval time, and the rate of change;
provide an analyte value range for the analyte values;
set a second interval time, the second interval time being
shorter than the first interval time, if the future analyte value is outside the analyte value range, and
longer than or equal to the first interval time, if the future analyte value is within the analyte value range; and
receive, via the receiver unit, one or more following analyte values in intervals of time for which the second interval time is applied.

19. A method of operating a continuous analyte monitoring system including a biosensor detecting present analyte values, and a receiver receiving present analyte values from the biosensor at determined interval times, the method comprising:

transmitting analyte values from the biosensor to the receiver at a first interval time;
receiving in the receiver present analyte values transmitted from the biosensor;
determining a rate of change for the analyte values;
determining a future analyte value based on the present analyte values, the first interval time, and the rate of change;
determining an analyte value range for the analyte values;
determining whether the future analyte value is within or outside the analyte value range;
setting a second interval time shorter than the first interval time if the future analyte value is outside the analyte value range, or setting a second interval time longer than or equal to the first interval time if the future analyte value is within the analyte value range; and
following the setting of the second interval time, transmitting present analyte values from the biosensor to the receiver at the second interval time.

20. The method of claim 19 wherein the receiver includes a controller determining the interval time based on the present analyte values, the first interval time, and the rate of change.

\* \* \* \* \*